(12) United States Patent
Davis et al.

(10) Patent No.: US 8,967,151 B2
(45) Date of Patent: Mar. 3, 2015

(54) AMBULATORY THERAPEUTIC FOOTWEAR

(76) Inventors: William Davis, Utica, MN (US); Keith Walli-Ware, Burnsville, MN (US)

( * ) Notice: Subject to any disclaimer, the term of this patent is extended or adjusted under 35 U.S.C. 154(b) by 582 days.

(21) Appl. No.: 11/904,561

(22) Filed: Sep. 27, 2007

(65) Prior Publication Data

US 2009/0084390 A1 Apr. 2, 2009

(51) Int. Cl.
*A61F 5/37* (2006.01)
*A61F 5/00* (2006.01)
*A61F 5/01* (2006.01)

(52) U.S. Cl.
CPC .................................. *A61F 5/0111* (2013.01)
USPC .............................. 128/882; 602/27; 602/23

(58) Field of Classification Search
CPC ... A61F 5/0111; A61F 5/0104; A61F 5/0102; A61F 5/0113; A61F 5/01
USPC ............................ 602/27, 28, 65, 23; 128/882
See application file for complete search history.

(56) References Cited

U.S. PATENT DOCUMENTS

| | | | | |
|---|---|---|---|---|
| 3,511,233 A | * | 5/1970 | Holy, Jr. ........................ | 128/892 |
| 3,713,437 A | * | 1/1973 | Wiedmer ....................... | 601/27 |
| 4,495,715 A | * | 1/1985 | Fredrickson et al. ........... | 36/113 |
| D326,556 S | | 6/1992 | Rooke et al. | |
| 5,372,576 A | * | 12/1994 | Hicks .............................. | 602/27 |
| 5,449,339 A | * | 9/1995 | Drennan ......................... | 602/23 |
| 5,501,659 A | * | 3/1996 | Morris et al. ................... | 602/27 |
| 5,603,692 A | * | 2/1997 | Maxwell ......................... | 602/28 |
| 5,906,206 A | * | 5/1999 | Shaw et al. .................... | 128/882 |
| 6,848,200 B1 | * | 2/2005 | Westin ............................. | 36/29 |
| 6,866,043 B1 | * | 3/2005 | Davis ............................. | 128/842 |
| 6,945,944 B2 | * | 9/2005 | Kuiper et al. ................... | 602/13 |
| 7,294,114 B1 | * | 11/2007 | Clement et al. ................ | 602/23 |
| 2005/0145256 A1 | * | 7/2005 | Howard et al. ............... | 128/882 |
| 2007/0149912 A1 | * | 6/2007 | Flam et al. ..................... | 602/61 |
| 2009/0076427 A1 | * | 3/2009 | Ponsi et al. .................... | 602/27 |

* cited by examiner

*Primary Examiner* — Victoria J Hicks
(74) *Attorney, Agent, or Firm* — DL Tschida

(57) ABSTRACT

A therapeutic fabric boot that warms the calf and foot, permits ambulation and provides for moisture absorption and selective exposure and ventilation of the covered extremity. An internal foam cradle restricts foot movement and reduces pressure at the heel and calf when lying in a supine position. A re-sizable, flat, hinged foam extension piece extends from the cradle and folds to protect the heel, sole and toes. Several fleece and moisture absorbent fabric cover panels selectively fasten about the foot and calf. Numerous hook and loop fasteners are fitted to external surfaces and attach to straps and/or outer cover pieces upon wrapping the straps and panel pieces about the supported lower calf and foot.

12 Claims, 16 Drawing Sheets

AMBULATORY THERAPEUTIC FOOTWEAR

BACKGROUND OF THE INVENTION

The present invention relates to medical footwear and, in particular, to an improved ventilated, fabric boot containing a molded foam, calf and heel support with an integrated folding sole and toe piece mounted in an insulated fabric covering and wherein hook and loop fasteners and straps are mounted to selectively expose, ventilate and relieve moisture and contact pressure at a protected extremity.

A variety of leg and footwear appliances have been developed for patient therapy situations. Pre and post-operative footwear are worn to prevent vasoconstriction and promote vasodilation to maintain blood circulation and thereby prevent clotting. That is, by keeping the legs and feet warm, the blood vessels don't constrict and healthy blood flow is maintained. The footwear also physically protects and warms the legs and feet with minimal skin trauma (e.g. ulcerations, cracking and/or abrasions). Fleece-lined, hook and loop fastened boots of the foregoing type manufactured by applicant are disclosed at U.S. Pat. Nos. Des. 326,556 and 6,866,043.

The present improved footwear was developed to provide a therapeutic boot that warms the extremity, permits ambulation and provides moisture absorption. Most significant, the boot selectively permits exposure and ventilation of the covered extremity. The improved boot also supports the calf, heel and sole in a foam cradle having a flat posterior surface and a contoured anterior surface that prevents leg rotation and reduces pressure at the heel and calf when resting in a supine posture. A plantar, hinged foam sole piece extends from the cradle and can be cut to vary the boot size. The foam sole piece is hinged to the foam calf support and folds to protect the heel, sole and toes. The boot interior is faced with insulation and fleece. An alternative boot is faced with sections of smooth, porous, laminated, moisture absorbent fabric in the region of the calf. Numerous hook and loop fastener pieces are fitted to exterior cloth surfaces and attach to straps and/or fabric cover pieces upon wrapping the straps and cover pieces about a supported calf and foot.

SUMMARY OF THE INVENTION

It is accordingly a primary object of the invention to provide thermally insulated medical footwear to stimulate blood circulation.

It is a further object of the invention to provide pre and post-operative footwear comprising a lined, thermally insulated, moisture wicking fabric boot having a number of hook and loop fasteners fitted to boot panel pieces and associated straps to collectively wrap and fasten to configure the boot about the leg and foot.

It is a further object of the invention to provide a fleece and laminated, porous moisture wicking fabric lined boot with a foam insert to define a flat posterior surface and a contoured interior surface that supports the calf and heel to prevent rotation and minimize heel support pressure when resting in a supine posture.

It is a further object of the invention to provide a foam support having a conformal contoured anterior surface that supports the calf and elevates the heel to reduce pressure at the heel when resting in a supine posture.

It is a further object of the invention to provide a foam support having a seamless, hinged plantar extension piece that can be cut to size and that wraps to encase the heel sole and toes.

It is a further object of the invention to provide a boot with fleece and/or porous, moisture wicking liner pieces that overly and contain a foam support(s).

It is a further object of the invention to provide a boot with panel pieces that permit selective exposure of portions of the foot and/or calf to inspection and ventilation without disruption to other panels.

It is a further object of the invention to provide an accessory wedge piece that mounts to the boot to support the foot against rotation.

It is a further object of the invention to provide straps that wrap around the metatarsal heads and attach to the boot to support the toes and prevent "foot drop" and accommodate swelling or bulky bandaging or dressings.

The foregoing objects, advantages and distinctions of the invention are obtained in a presently preferred fabric boot of the invention that is lined with thermal insulation, fleece and/or porous, laminated fabric. The laminated fabric is constructed and located to enhance the wicking of moisture and ventilation of the foot. Several tabs of hook and loop fastener materials are arrayed about several fabric panel pieces that mate with other associated panel pieces and straps. The straps and panel pieces align to define and selectively control the fitting of the boot to the foot. The panel pieces are shaped and located to permit selective exposure of portions of the foot without disrupting adjoining panel pieces that cover other portions of the foot to permit inspection and ventilation.

A contoured foam calf and heel support mounts within the boot. Ventilation apertures can be formed in the foam support. A posterior surface of the support exhibits a flat surface portion that prevents leg rotation. A longitudinal interior surface of the support is contoured to conform to the calf, elevate the heel and distribute leg weight to prevent pressure points, especially at the heel. The calf support is contained between the external fabric cover and an internal liner.

A foam plantar extension piece is fastened and hinged to the calf/heel support at a recessed pocket. A closed cell portion of the extension piece is covered with an open cell foam piece and fleece and/or fabric materials. Lateral flaps or wings project from the sides of the covered extension piece to overlap the foot. The wings are secured to permit selective exposure and/or ventilation of the foot without disrupting other, separately fastened panel pieces. The extension piece folds to protect the heel, sole and toes and along with the associated wing panel pieces can be trimmed and re-sized.

Hook and loop fasteners are secured to external and internal panel surfaces and are aligned to overlap and secure the boot to the foot. An accessory wedge piece fastens to the external cover to prevent leg and/or foot rotation. Other accessory and extension straps mount to the external cover to prevent foot drop and accommodate swelling and/or bulky bandaging or dressings.

Still other objects, advantages, distinctions and constructions of the invention will become more apparent from the following description with respect to the appended drawings. Similar components and assemblies are referred to in the various drawings with similar alphanumeric reference characters. The description should not be literally construed in limitation of the invention. Rather, the invention should be interpreted within the broad scope of the further appended claims.

Figure 1:
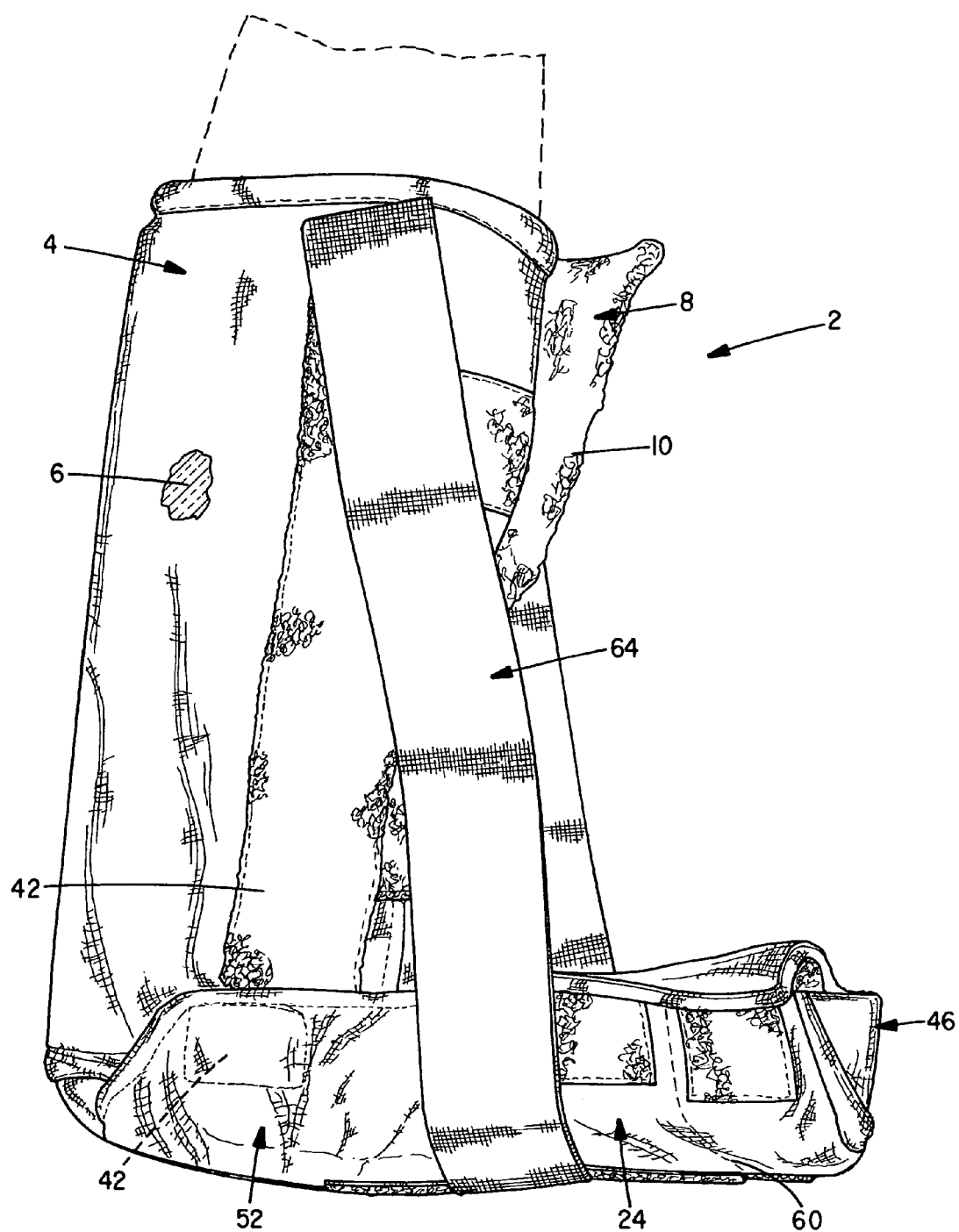
FIG. 1 is a right side perspective drawing of the boot shown in an upright position with the boot wrapped to a closed condition about the leg of a wearer (shown in dashed line) and a foot drop strap mounted to the cover.
Figure 2:
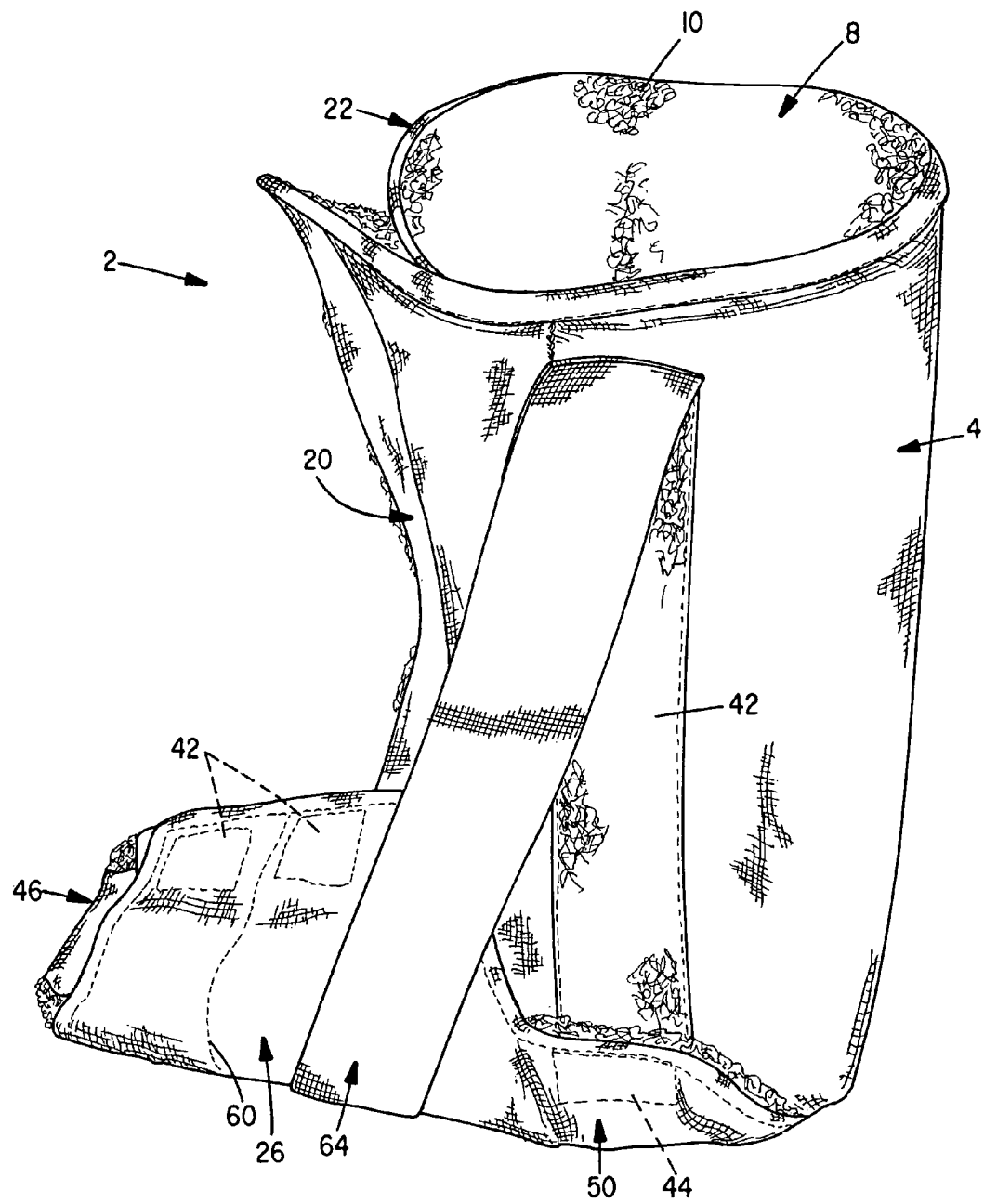
FIG. 2 is a left side perspective drawing of the boot with the boot wrapped to a closed condition and a foot drop strap mounted to the cover.
Figure 3:
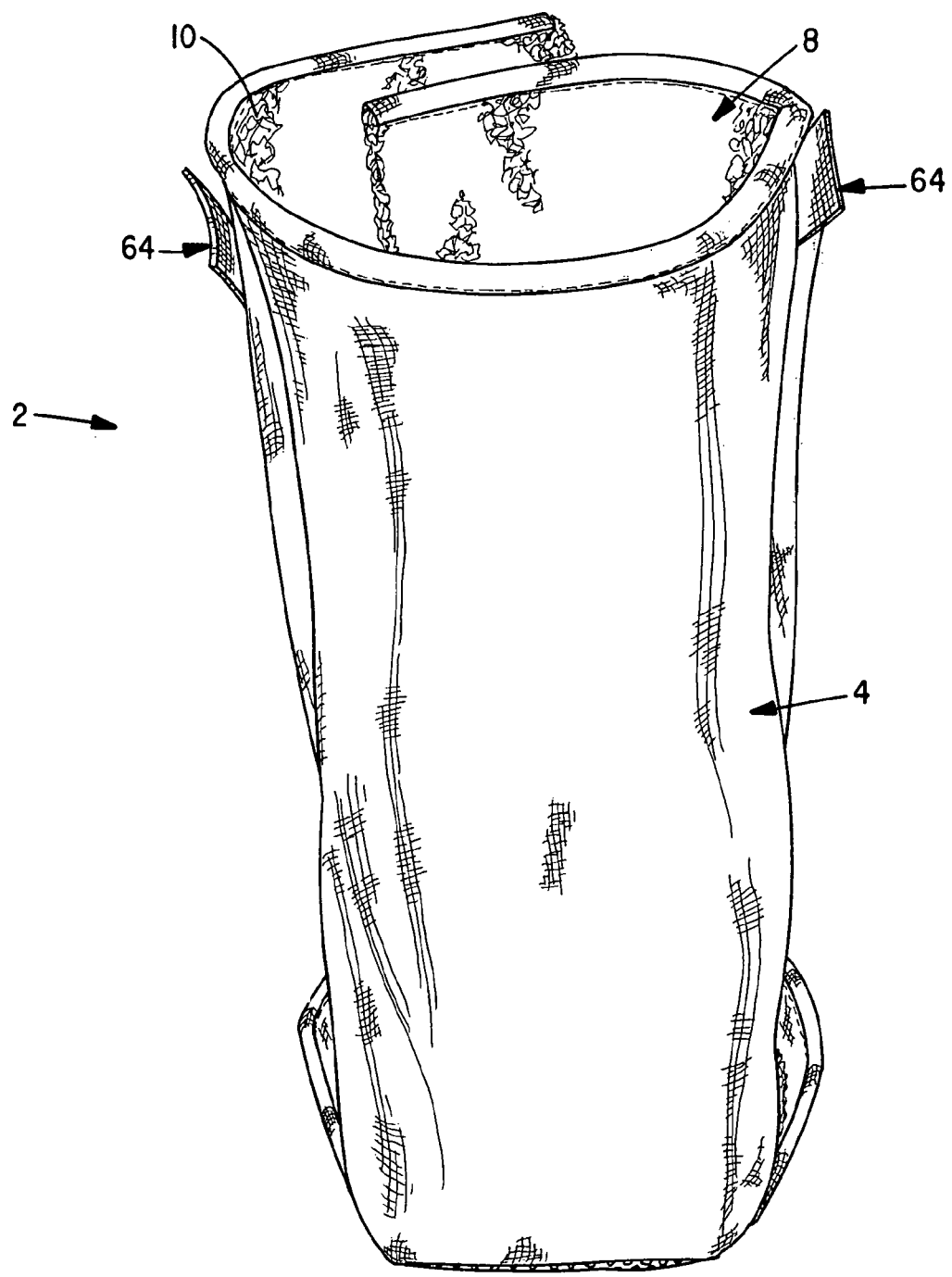
FIG. 3 is a rear perspective drawing of the boot with the boot wrapped to a closed condition and a foot drop strap mounted to the cover.
Figure 4:
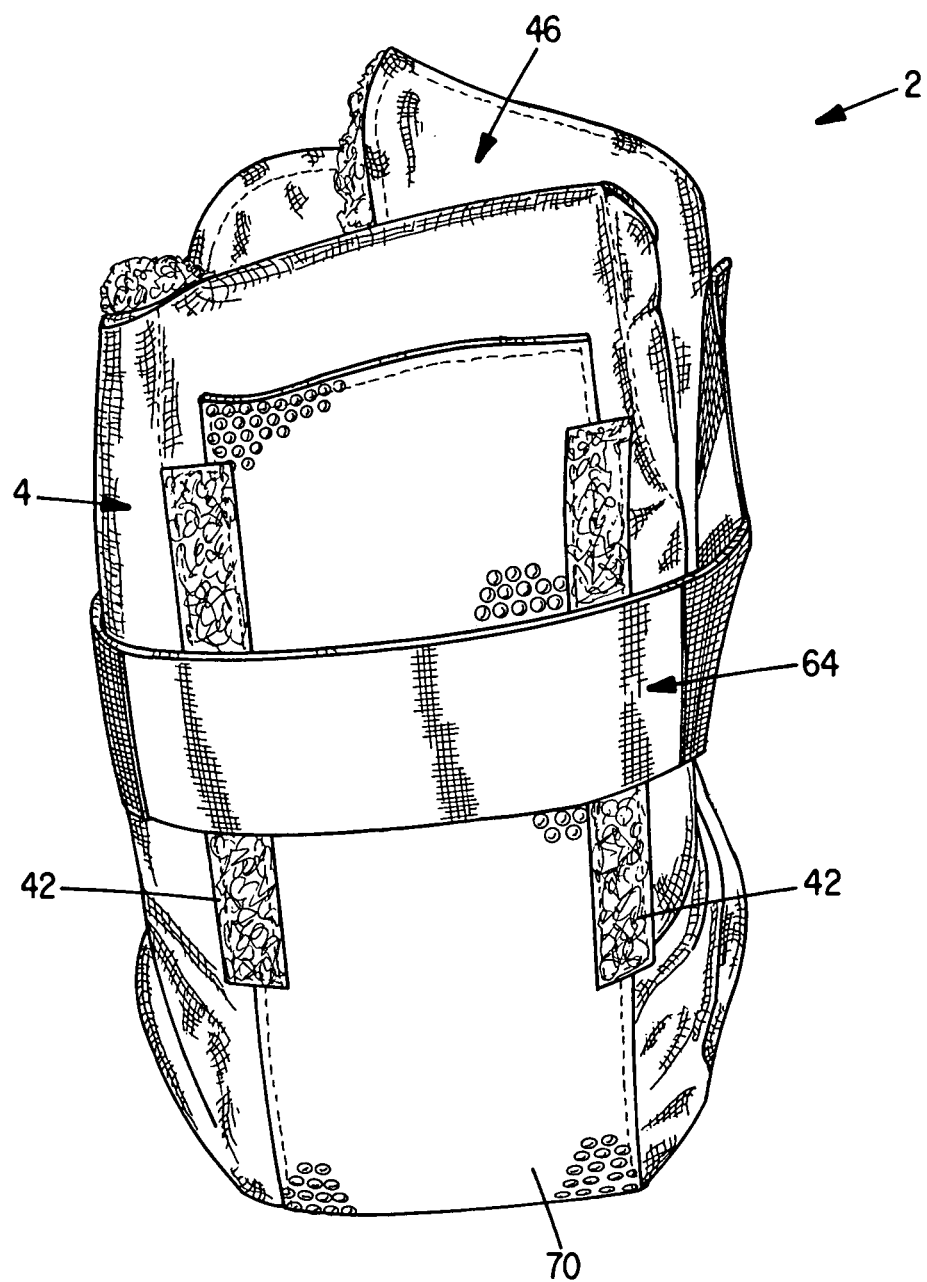
FIG. 4 is a bottom perspective drawing of the boot with the boot wrapped to a closed condition and a foot drop strap mounted to the cover.
Figure 5:
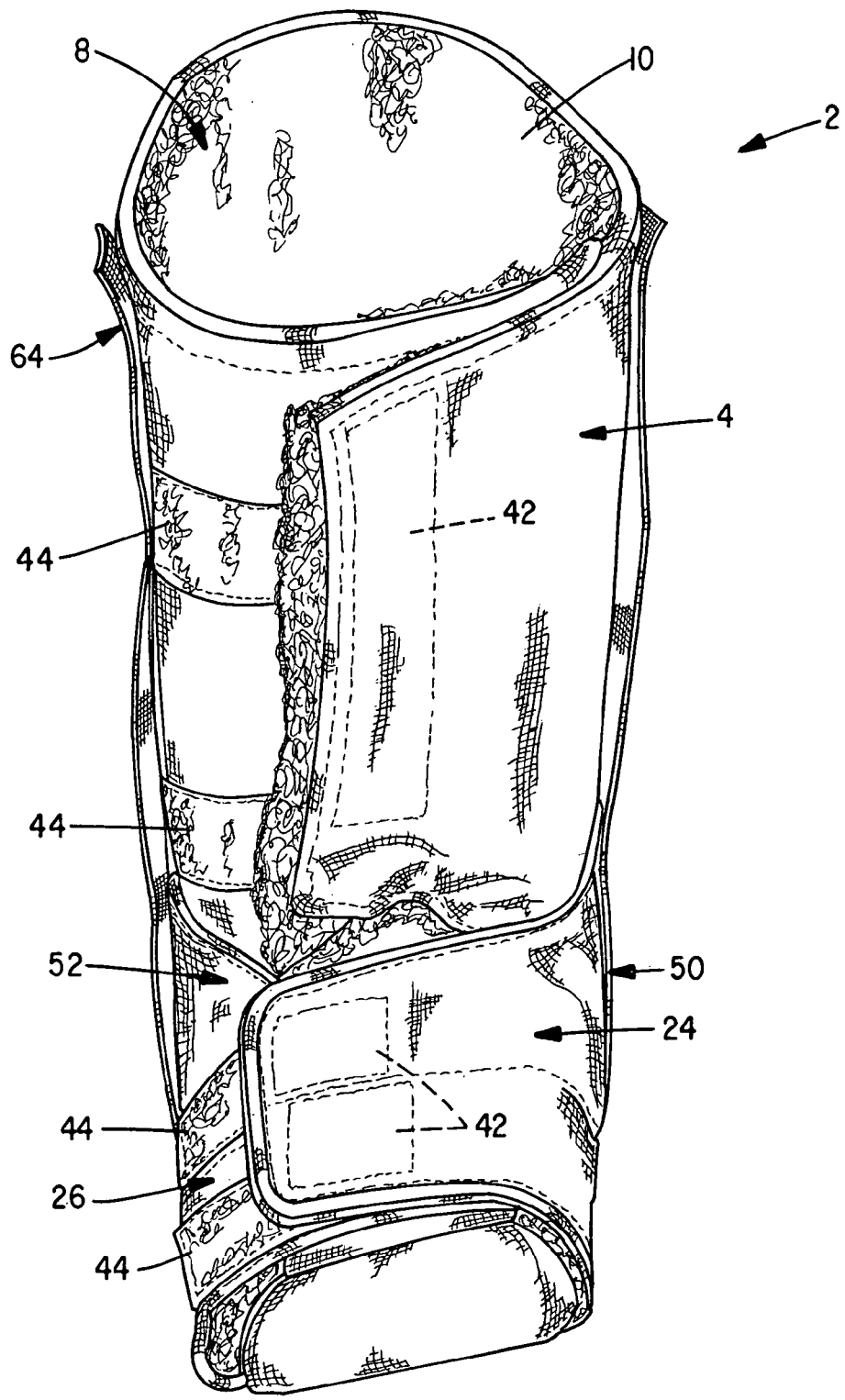
FIG. 5 is a front perspective drawing of the boot with the boot wrapped to a closed condition and a foot drop strap mounted to the cover.

Similar structure throughout the drawings is referred to with the same alphanumeric reference numerals and/or characters.

DESCRIPTION OF THE PREFERRED EMBODIMENT

Referring to FIGS. 1-5 several perspective views are shown to external surfaces of the improved therapeutic boot 2 of the invention. The boot 2 is constructed of an air permeable, fabric cover 4. The cover 4 is presently sewn from a durable velour cloth. Other materials such as a heavyweight cotton fabric, CORDURA® or other fabrics or fabric combinations might also be used.

A thermal insulation material 6 (shown in cutaway) is fitted between the cover 4 and a separate interior lining 8. The insulation material 6 can comprise THINSULATE® or any of a variety of other suitable thermal insulation materials. The insulation material 6 provides a thermal barrier to maintain the temperature of the calf and foot to promote dilation of the blood vessels and blood flow through the covered extremity.

Figure 6:
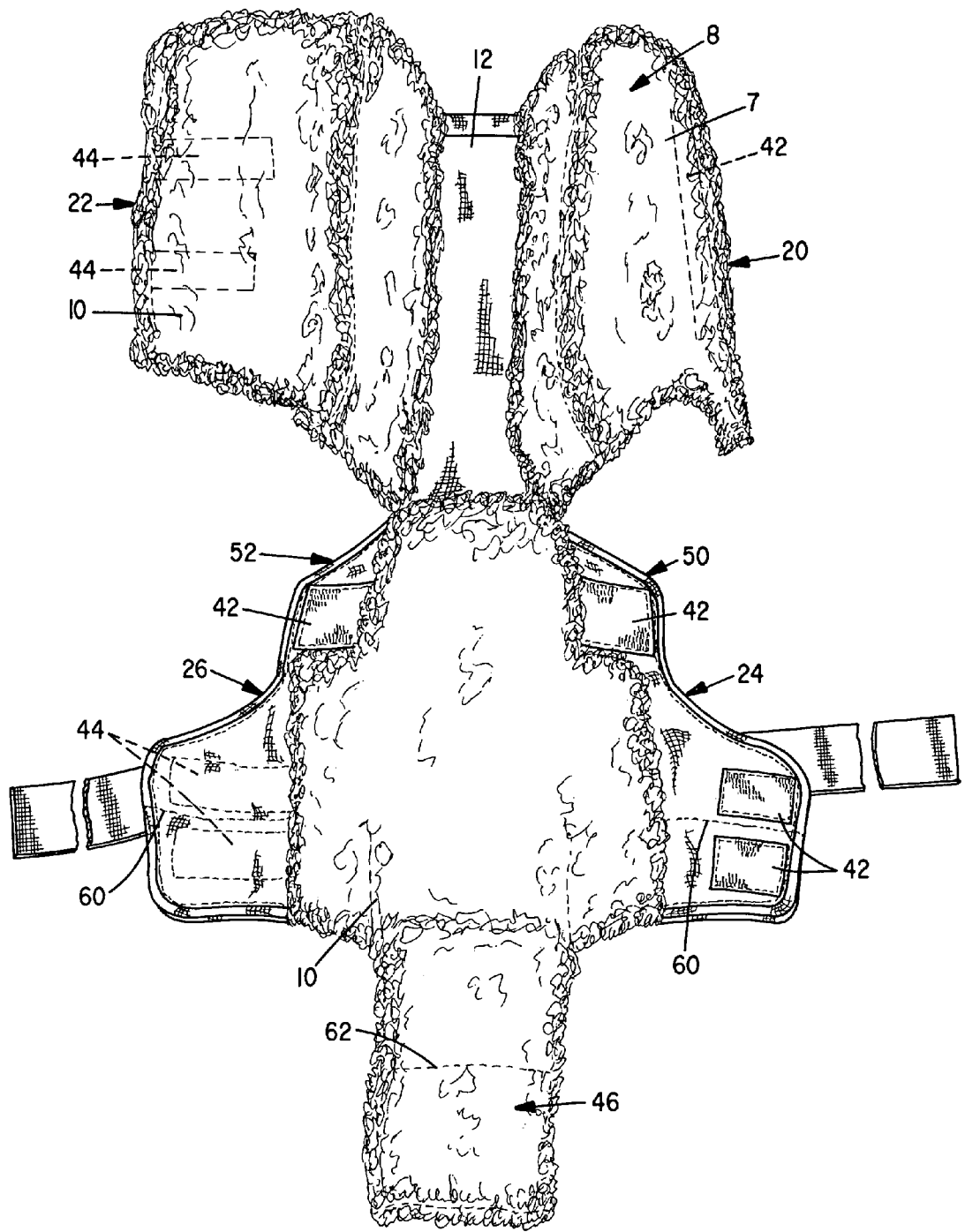
FIG. 6 is a front perspective drawing showing the calf and plantar, heel/sole/toe extension pieces and lateral overlapping wing panel pieces folded open and detached from the calf support panels.
Figure 7:
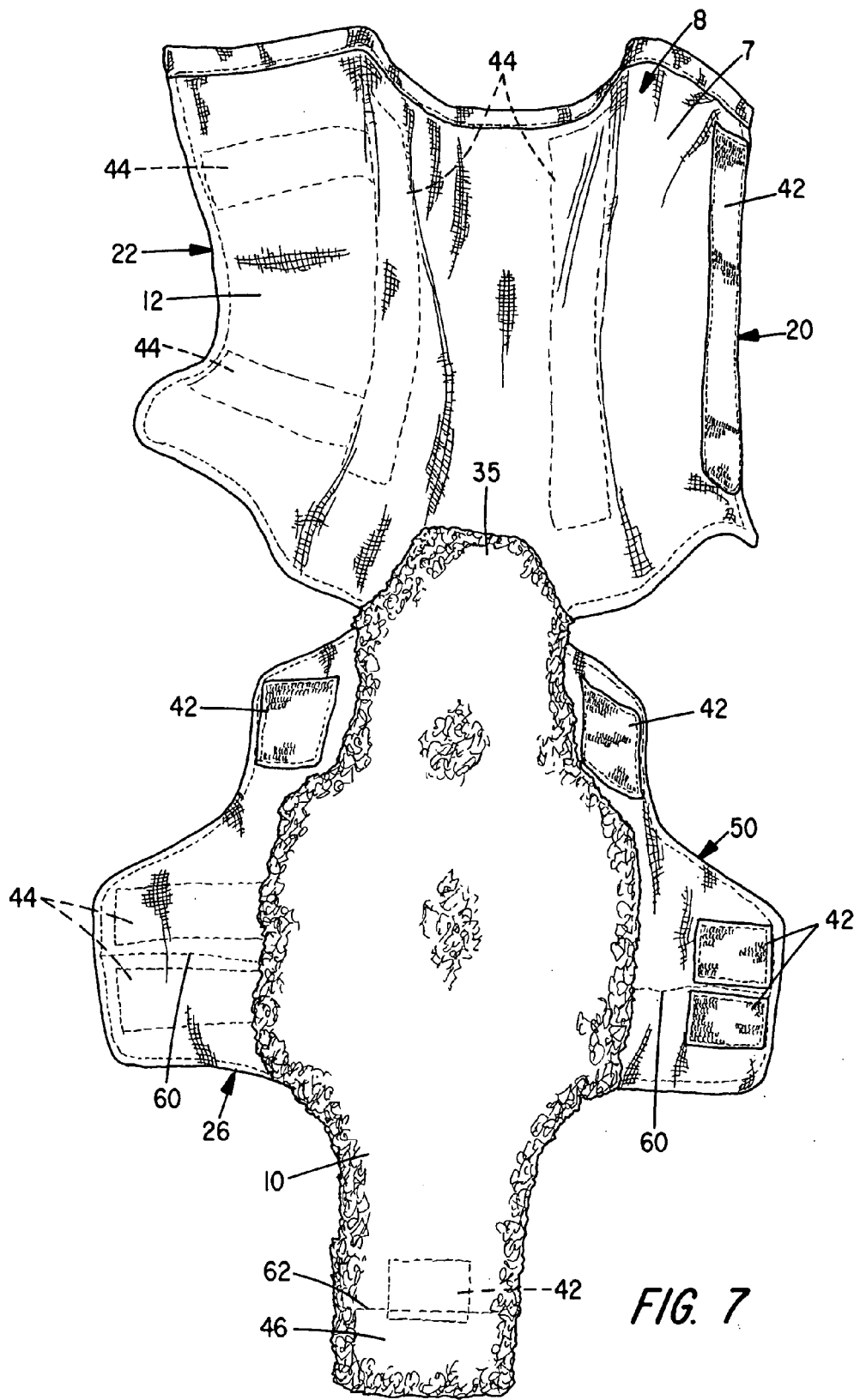
FIG. 7 is a front perspective drawing showing an alternative construction of the boot liner wherein a porous, moisture wicking liner covers the calf and heel support surfaces of the boot.
Figure 9:
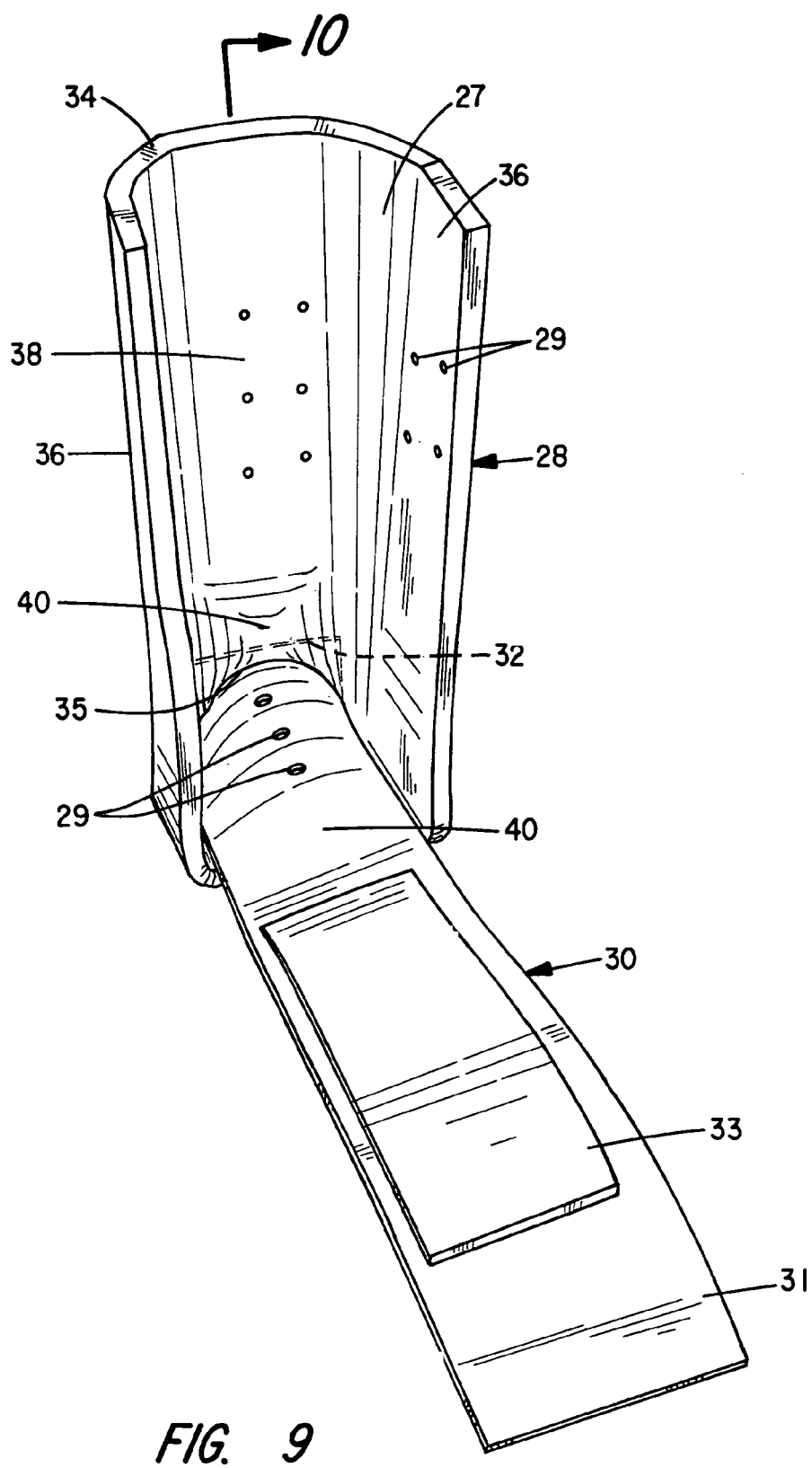
FIG. 9 is a front perspective drawing showing the foam calf cradle support and foam plantar heel/sole/toe extension piece removed from the boot.

With additional attention to FIGS. 6, 7 and 9, the lining 8 is constructed and organized to provide a soft, smooth/comfortable surface to contact the skin without any abrading seams or surface portions that can cause ulcerations or skin trauma. The lining 8 is also constructed to provide a soft interface with the calf and foot to wick moisture away and ventilate the covered calf and foot. Seams between sections of fleece 10 and/or fabric, moisture wicking materials 12 are located and configured to minimize contact with the skin. Seams can be sewn or adhesively fixed.

Seams in the region of the heel are especially avoided or hidden in the boot 2. Presently, an adhesively bound seam between calf and extension liner pieces at the heel is located in or immediately adjacent a recess 32 of a foam support cradle 28. The recess 32 shelters overlapping or butted, adhesively bound liner pieces. The recess 32 also shelters the proximal end of a foam, plantar extension piece 30 that extend from the support cradle 28. regions of sustained contact between the skin and the lining 8.

For the boot 2 of FIG. 6, the fleece material 10 comprises the entire liner 8 and is located to surround the calf and foot. As with the boot 2 of FIG. 7, the insulation 6 is generally included beneath all regions of the lining 8 to surround the entire calf and foot, although could be selectively positioned about the boot 2. Collectively, the insulation 6 and fleece material 10 traps warm air and wicks away moisture.

The interior lining 8 of the boot 2 of FIG. 7 otherwise is constructed of several sections of fleece material 10 and/or moisture wicking materials 12. The moisture wicking material 12 used in the boot of FIG. 7 presently comprises a material having a porous, center substrate piece and to the opposite surfaces of which micro-fleece materials are laminated. The side facing the interior of the boot 2 is covered with an open-weave and/or porous polyester facing piece (e.g. such as used in sports clothing). The facing piece is smooth and apertures in the material ventilate the material and foot against and any absorbed moisture. A variety of other soft, moisture absorbent, air permeable open weave or porous materials can be used.

The wicking material 12 is located to absorb moisture and ventilate the foot. Moisture typically develops at regions of sustained contact between the skin and the lining 8. The moisture wicking material 12 is preferably located at the primary points of contact with the calf and foot, for example, at the posterior surfaces of the calf, at the heel, sole and around the foot.

The boot 2 of FIG. 7 only surrounds the calf with the foregoing laminated moisture wicking materials 12. Fleece 12 otherwise covers the foot and a layer of insulation 6 is provided below both materials 10 and 12. While FIGS. 6 and 7 depict two presently preferred configurations of the liner 8, the locations of the fleece 10 and moisture wicking material 12 can be varied as desired.

With additional attention to FIGS. 6 through 9, details are shown to the construction of the boot 2 and the relative arrangement of several fabric panels that are or can be lined with the fleece 10 and/or moisture wicking material 12. FIGS.

Figure 10:
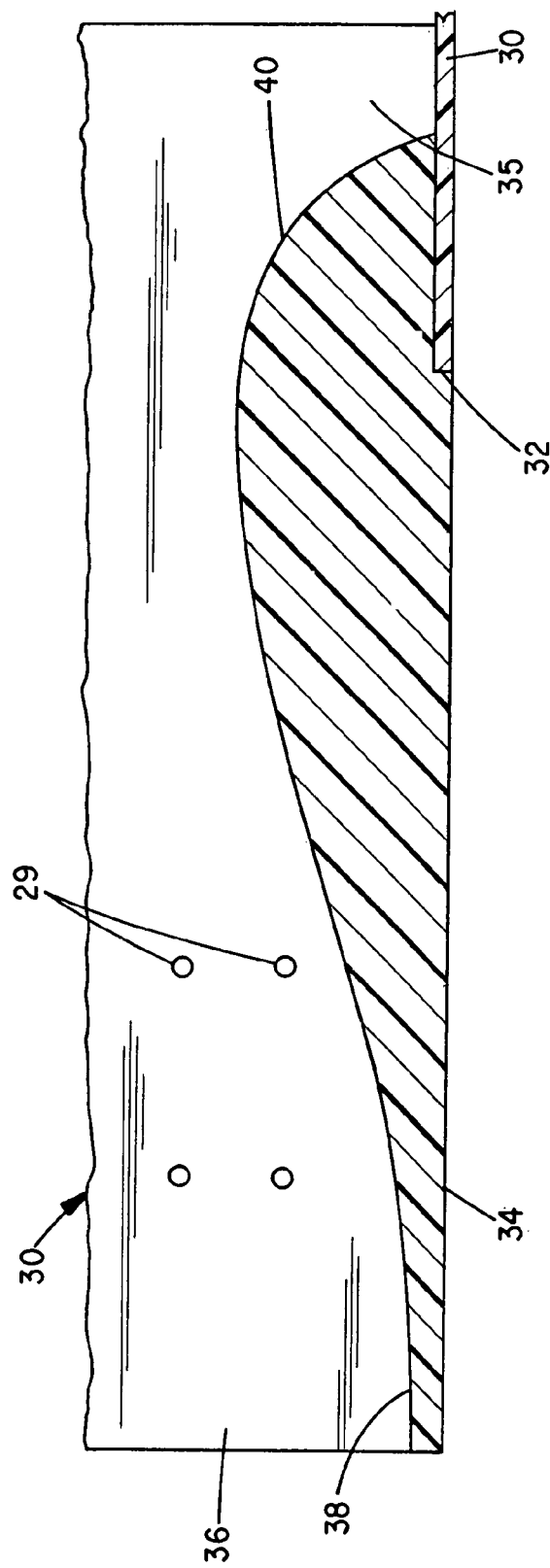
FIG. 10 is a longitudinal cross section drawing of the calf support cradle depicting the flat outer and contoured inner surfaces.
Figure 11:
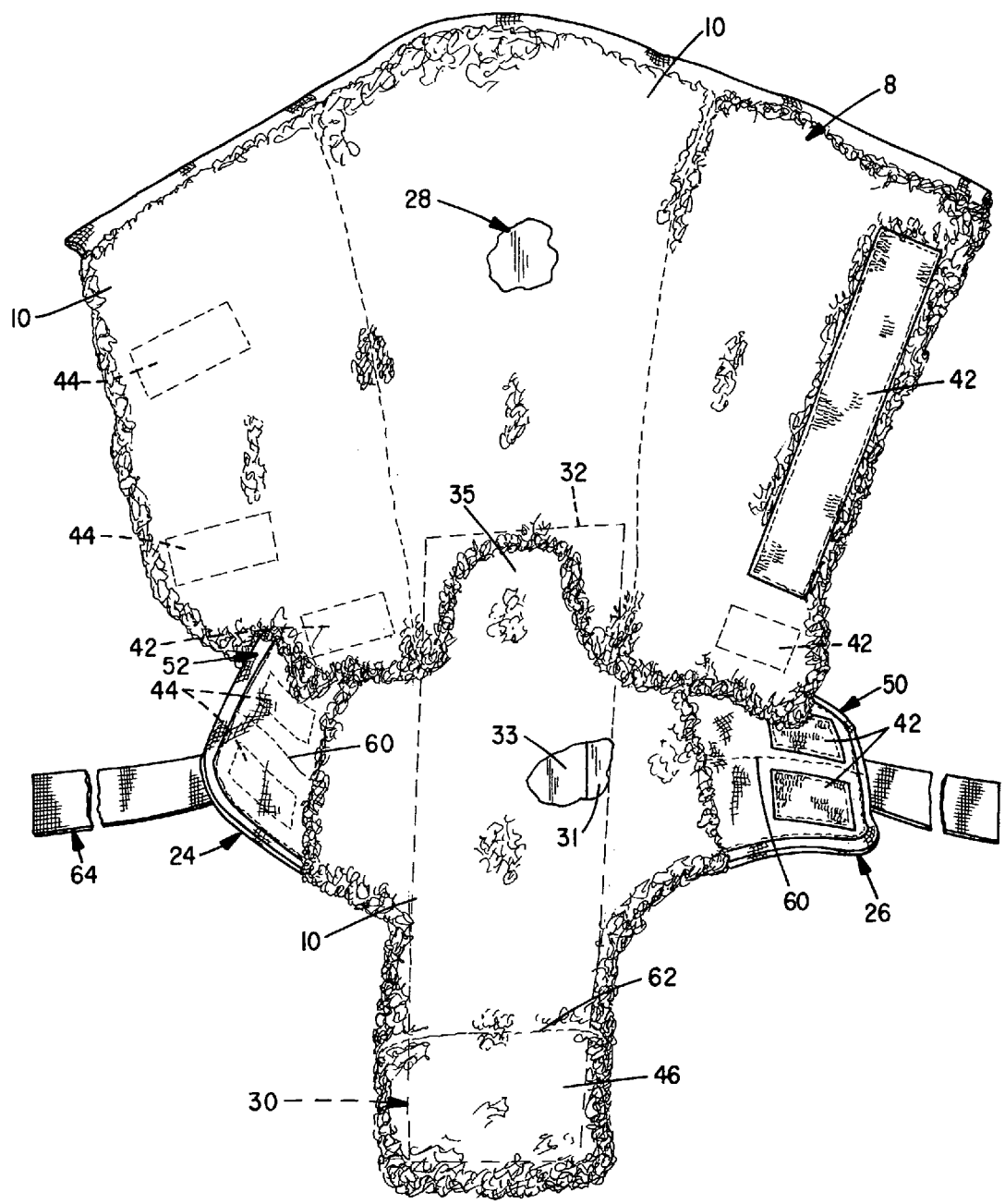
FIG. 11 is a front perspective drawing showing the heel/sole/toe extension piece and the overlapping wing panels folded open and wherein portions of the cradle piece and layers of the extension piece are shown in cutaway portions.
Figure 12:
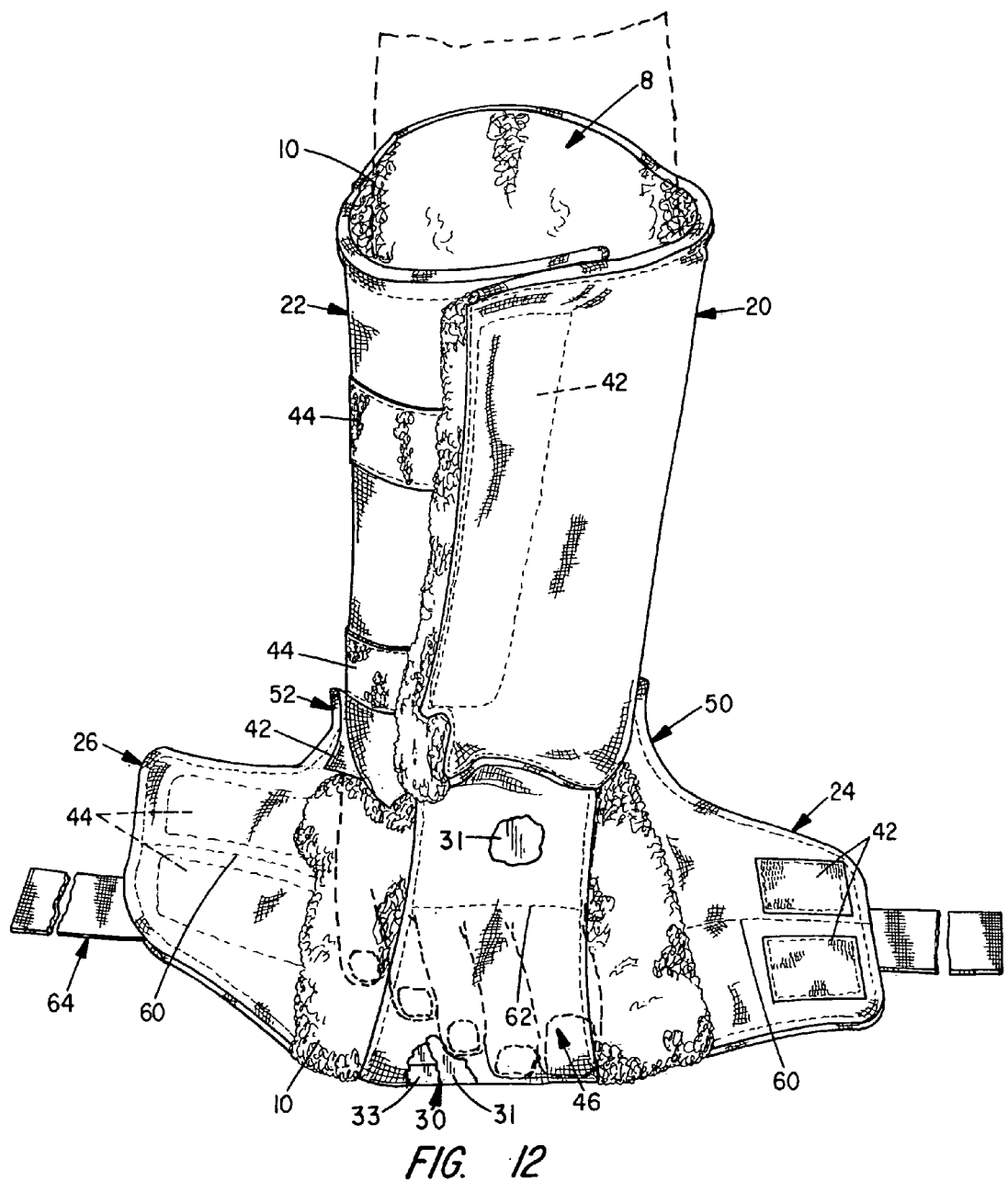
FIG. 12 is a front perspective drawing showing the toe portion of the plantar extension piece folded closed over a wearer's foot (shown in dashed line) and the adjacent overlapping wing panels folded open.

6 through 8 depict the interior and exterior construction of the boot 2 with the panels folded open. FIGS. 9 and 10 depict the foam support cradle 28 that mounts inside the boot 2 beneath the liner 8. FIGS. 11 and 12 depict the several boot panels as they are sequentially folded and fitted to the calf and foot to ultimately form the wrapped configurations shown at FIGS. 1 through 5.

Figure 8:
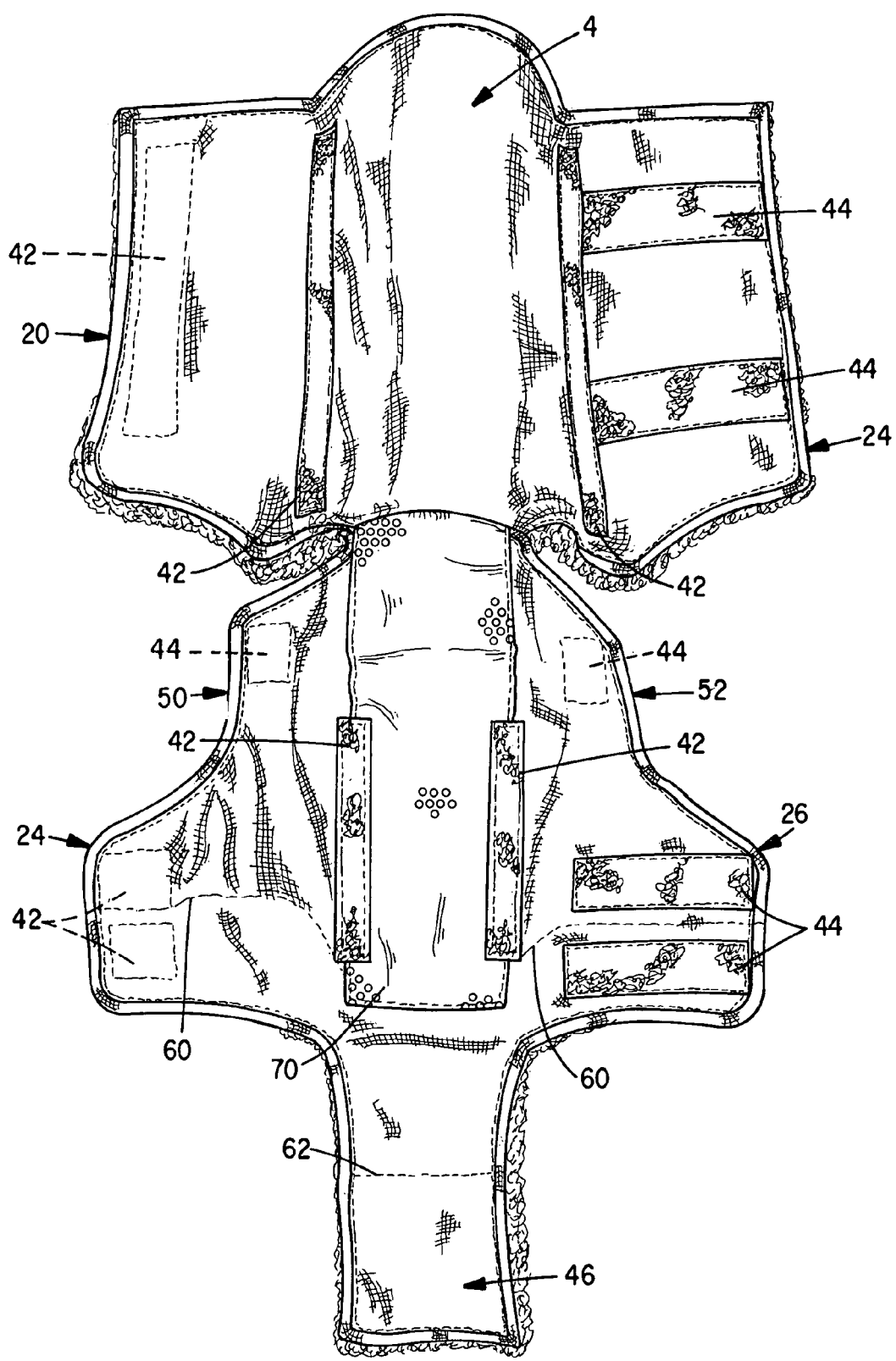
FIG. 8 is a rear perspective drawing showing the external surface of the boot folded open.

Apparent from FIGS. 6 through 8 are respective internal and external folded open views of the boot 2. The boot 2 opens full-length along its front or anterior surface at right and left, fleece covered calf panels 20 and 22 and right and left foot panels 24 and 26.

The calf panels 20 and 22 overly and contain the foam support cradle 28 shown in detail at FIGS. 9 and 10. The cradle 28 is preferably constructed of a relatively dense elastic material that flexes or compresses slightly to provide a resilient interface with the calf. The cradle 28 can for example be constructed of a variety of materials including elastomers, polyurethane foam, and/or other open and/or closed cell foams or combinations thereof. The durometer and resilience of the material preferably compresses slightly to support the calf and foot without undue compression, yet springs back to shape upon relieving any pressure, particularly at the anterior surface of the calf.

The cradle 28 provides a longitudinal channel 27 that receives the calf. The cradle 28 mounts in a pocket or space formed beneath and between the calf panels 20 and 22. The cradle 28 can provide through apertures 29 to aerate the calf. The foot panels 24 and 26 overly and contain a separate flat, foam plantar extension piece 30. A base portion 31 of the extension piece 30 is constructed of a closed cell foam, approximately ⅛-inch thick. A proximal end is bonded to a recess 32 (shown in dashed line) formed into the flat posterior surface of the support cradle 28 adjacent an inverted U-shaped cutout 35 adjacent the peripheral edge of the anterior surface of the cradle 28. The cutout 35 is formed to shelter the suspended heel as described in more detail below. Peripheral edges of the cutout 35 arcuately depend to contact the extension piece 30, reference FIG. 10.

Any seam between the cradle 28 and extension piece 30 is thereby removed and/or shielded by the recess 32 and cutout 35 from contact with the heel. The plantar extension piece 30 extends from the region adjacent the heel and wraps over the sole and toes. An interior surface of the extension piece 30 is typically covered with a separate panel of open celled foam 33 approximately ½-inch thick. The plantar extension piece 30 and portions of the overlapping panels 24 and 26 are also fabricated to be sheared to size when the boot 2 is first fit to a user and the details to which fitting are discussed below. The extension piece 30 includes vent apertures 29 in the region of the heel.

With attention also to FIGS. 9 and 10, the support cradle 28, when viewed from a longitudinal end, generally exhibits a U-shape. A posterior surface 34 of the cradle 28 is constructed to be flat and from which side walls 36 project and extend along the longitudinal sides of the calf. The flat surface 34 stabilizes the cradle 28 and calf against rotation when the user rests in a supine position and the boot 2 is supported on a bed.

The anterior surface 38 of the cradle along the channel 27 is contoured and exhibits a compound arcuate shape to support the calf, reference FIG. 10. A raised surface portion 40 in the region of the Achilles tendon is shaped to elevate and support the heel in the cutout region 35 with minimal pressure and contact with the boot and away from any support structure, such as a bed, foot stool etc.

Figure 16:
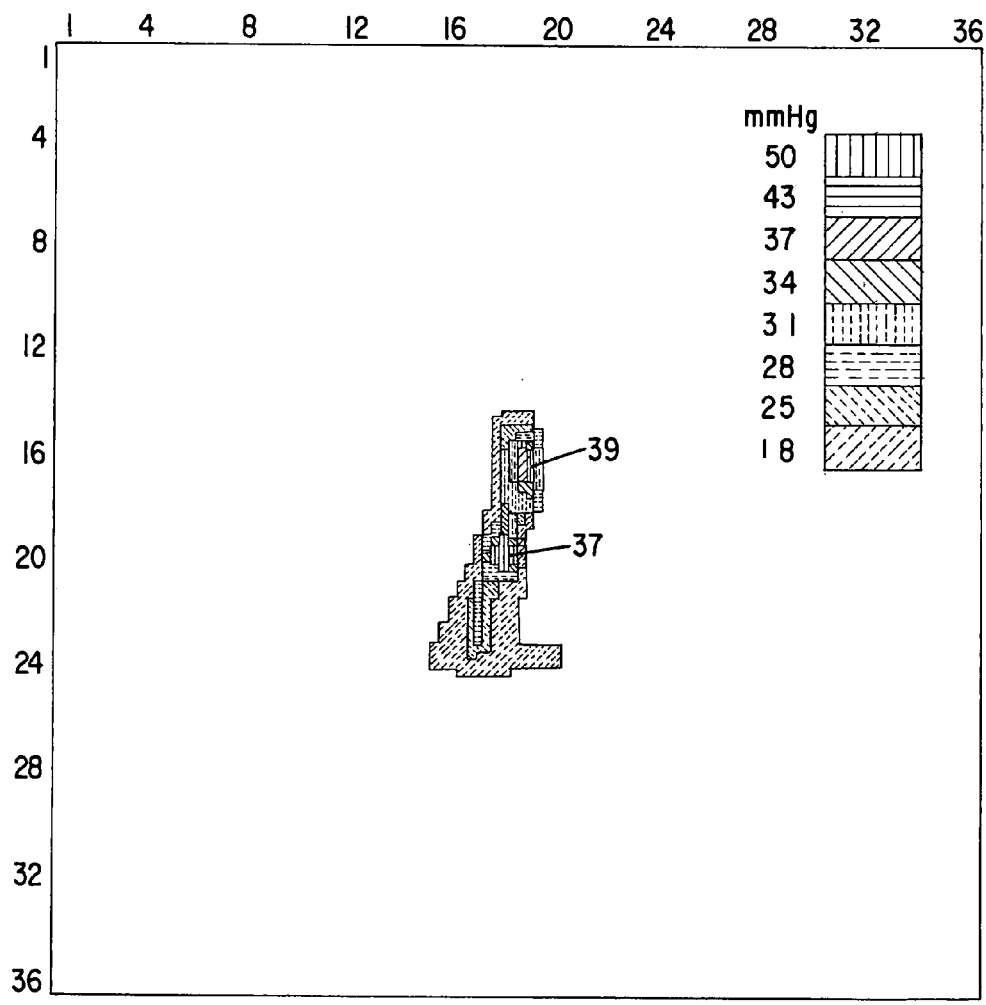
FIG. 16 is a pressure map drawing showing the foot pressure of a prior art boot having an average pressure distribution of 16 mmHg and several peak pressure points on the order of 62 mmHg.
Figure 17:
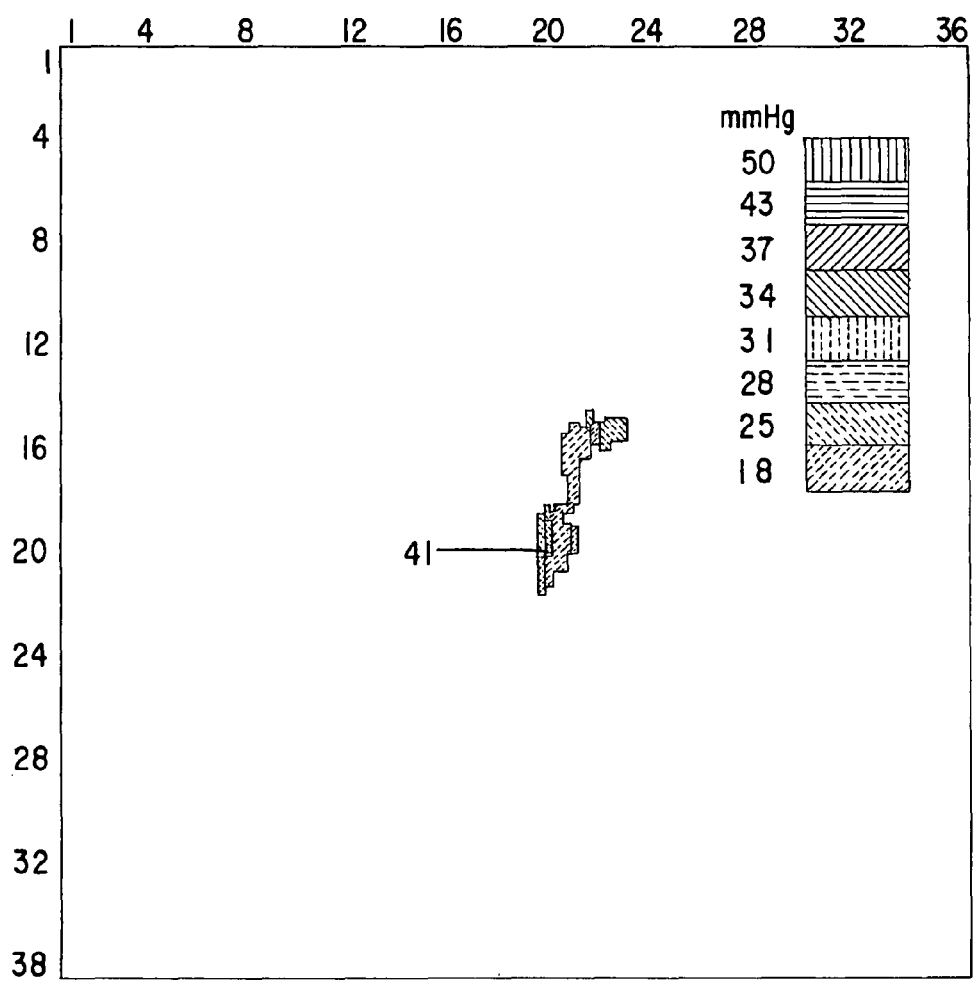
FIG. 17 is a pressure map drawing showing the foot pressure of the improved boot of the invention with a reduced, evenly distributed pressure profile on the order of 14 mmHg and a minor peak pressure of 28 mmHg.

The contoured surfaces 38 and 40 are particularly formed to distribute and equalize support pressures on the calf and prevent pressure points that might induce skin ulceration or abrasion. FIG. 16 depicts a pressure map to a prior boot of applicant that exhibited an average pressure distribution of 16 mmHg and two relatively significant pressure points 37 and 39 on the order of 62 mmHg. FIG. 17 in contrast depicts a pressure map to the improved boot 2 of the subject invention which uses the cradle 28 and plantar extension piece 30 and wherefrom a reduction of pressure points and even distribution of pressure on the order of 14 mmHg average and a minor peak pressure point 41 of 28 mmHg is apparent. The latter pressures are well below the nominal pressure of 32 mmHg where capillary closure and reduced blood perfusion and flow is observed with consequent risks of skin ulceration Returning attention to FIGS. 6 through 8 and when folded closed, the calf panels 20, 22 and foot panels 24, 26 respectively wrap and overlap each other to form the boot 2 shown at FIGS. 1-5. The overlapped panels 20-26 are fastened together with mating strips of hook 42 and loop 44 type fastener material aligned along the peripheral edges of the panels 20-26. Hook and loop fasteners 42 and 44 are preferred although other fastenings might be adapted to the boot 2.

In the region of the foot, several parallel strips of hook fastener material 42 are sewn to extend in displaced, transverse relation along the edge of the panel 24 to overlap and mate with several transverse strips of loop fastener material 44 located along the edge of the panel 26. The overlapped panels 24 and 26 cover a toe panel 46 defined by a distal end of the extension panel 30 that folds to cover the toes.

The calf panel 20 separately contains spaced, transverse strips of loop material 44 along the edge of the panel 22 that overlap and mate with a longitudinal strip of hook fastener material 44 that extends along the longitudinal edge of the panel 20. When the panels 20 and 22 are wrapped around the calf and overlapped in the manner of FIG. 12, the strips of fasteners 42 and 44 bind the upper portion of the boot 2 to the calf at a desired, adjustable pressure.

Also apparent from FIGS. 6 through 8 are right and left heel panels 50 and 52. The panels 50 and 52 include tabs of hook material 42 that mate with the lower end of longitudinal strips of loop material that longitudinally extend along the approximate center of the panels 20 and 22. The heel panels 50 and 52 hinge the foot panels 24 and 26 to the calf panels 20 and 22. The heel panels 50 and 52 also advantageously facilitate a selective exposure of the heel during treatment. That is, the heel panels 50 and 52 can be detached independent of the foot and calf panels 20-26, either for inspection or for ventilation without disrupting the foot panels 20-26 to expose the heel area. This additional flexibility is very desirable to facilitate healing and ventilate and aerate the lining 8 to evaporate moisture. FIGS. 11 and 12 depict the hinge panels 50 and 52 secured to the cradle panels 20 and 22.

The boot 2 can also be re-sized to fit users with smaller feet. In this regard and from FIGS. 6 through 8, a number of seams of stitching 60 and 62 are respectively provided at the foot panels 24 and 26 and the toe panel 46. The stitching 60 and 62 permit a care giver to size the boot 2 to best fit the user. For patients with smaller feet, the distal portions of the toe and foot panels 46 and 24, 26 can be cut away or trimmed from the boot 2 to accommodate the smaller foot. The stitching 60 and 62 also prevents fraying at the remaining associated panel portions.

Where the flat posterior cradle surface 34 prevents foot rotation, a strap 64 shown at FIG. 12 is provided that can be secured to the longitudinal lengths of loop fastener material 42 at the cradle panels 24 and 26 and wrapped below the foot to prevent "foot drop", reference FIGS. 1-5 and 15. The interior surface of the strap 64 is covered with several tabs of hook material 44. The strap 64 attaches beneath the foot panels 24 and 26 to strips of looped fastener 42 that longitudinally extend along the sides of a traction pad 70 that is formed from non-slip material and sewn to the surface of the cover 4 in the region of the sole.

The pad 70 facilitates safe ambulation over smooth tile or wood floors. The pad 70 can be constructed of a variety of non-slip materials. The pad 70 is shaped to essentially align with and underlie the plantar extension piece 30. Upon wrapping the panels 20-26 and 46 over the foot, the strap 64 overlaps mating loop material and establishes the angle of the foot to the calf.

Figures 13, 14:
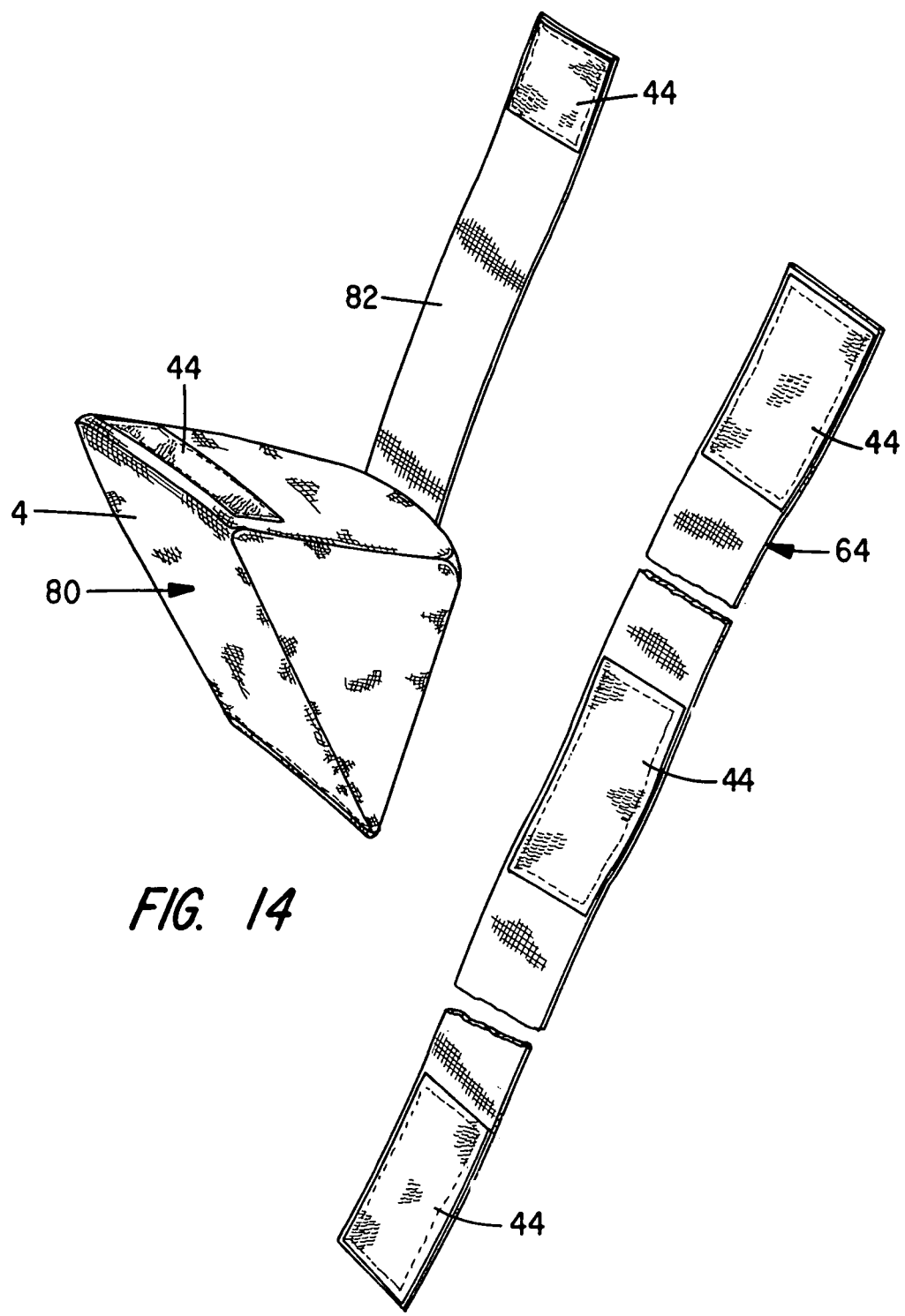
FIG. 13 is a perspective drawing showing a strap that mounts to the boot to prevent foot drop.
FIG. 14 is a perspective drawing showing an accessory wedge support piece that mounts to prevent foot rotation.
Figure 15:
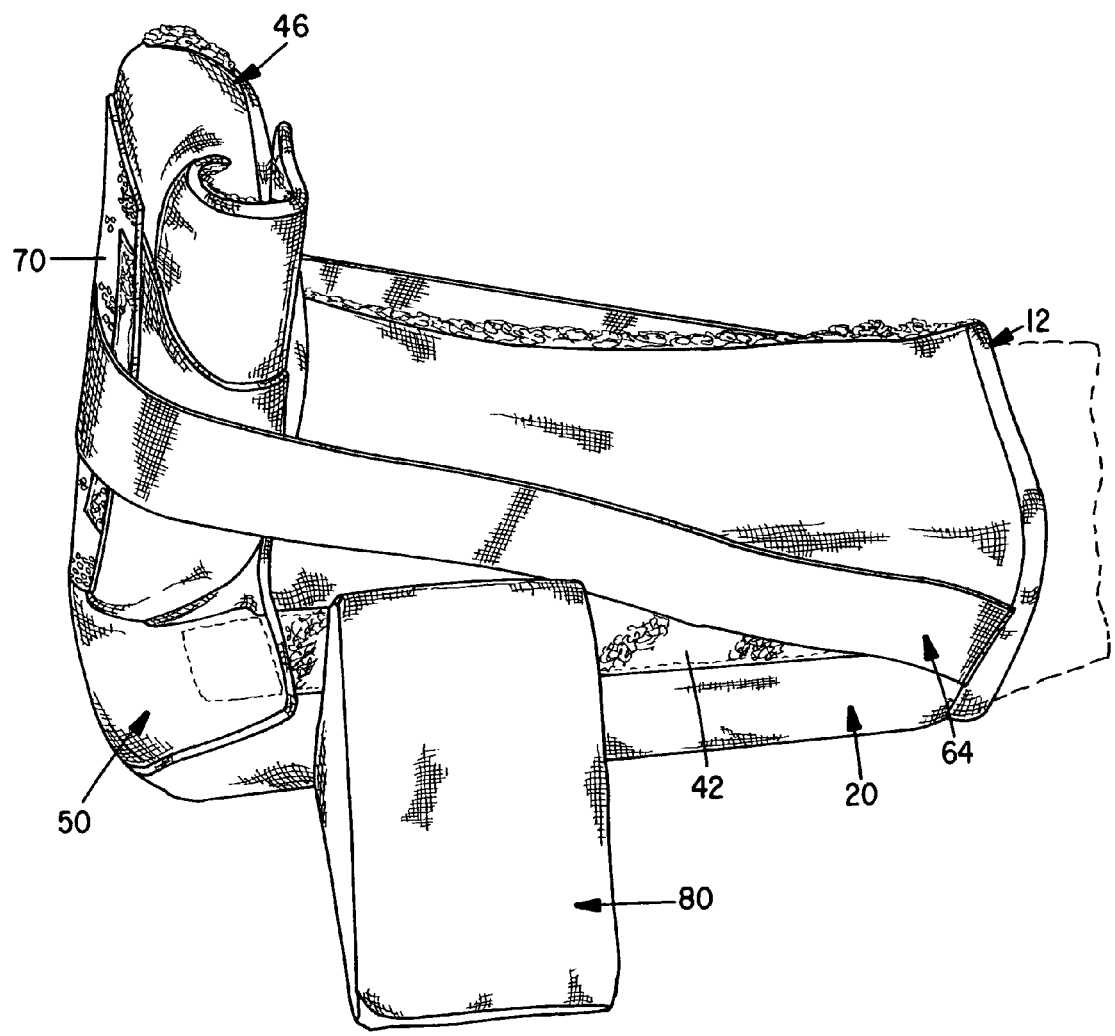
FIG. 15 is a perspective drawing showing the foot drop strap and accessory wedge as they appear when mounted to the boot and the foot of a supine wearer's leg (shown in dashed line).

The foot can be further supported with the benefit of an accessory wedge-shaped support 80 shown at FIG. 13. The support also prevents foot rotation. The support 80 is constructed of a right triangular piece of foam that is covered with the cover material 4. A tab of hook material 44 is secured to at least one of the exposed orthogonal surfaces and can fasten to the strips of loop material 42 that extend along the sidewalls of the calf panels 20 and 22.

A strap piece 82 and fastener tab 44 extend from the support 80 and can be trained beneath the calf panels 20 and 22 and fasten to strips of fastener 42 such as in the fashion shown at FIG. 14. The support 80 might also be fitted to axially align with the pad 70 and heel.

For users with relatively large feet, swelling or having bulky bandaging or dressings such that the foot panels 24 and 26 cannot overlap, an extension strap of suitable length and constructed similar to strap 64 can also be secured between the foot panels 24 and 26.

From the foregoing, it is to be appreciated the boot 2 advantageously protects and thermally insulates the foot and lower leg. The construction of the boot 2 provides numerous advantages and improvements over known therapeutic footwear. The subject footwear particularly protects the heel and foot, permits ambulation, warms and ventilates the foot and calf.

While the invention has been described with respect to a number of preferred constructions and considered improvements or alternatives thereto, still other constructions may be suggested to those skilled in the art. It is to be appreciated that selected ones of the foregoing features can also be used singularly or be arranged in different combinations to provide a variety of improved therapeutic footwear. The foregoing description should therefore be construed to include all those embodiments within the spirit and scope of the following claims.

What is claimed is:

1. Therapeutic footwear apparatus adapted to cover a wearer's leg comprising:
   a) a boot comprising a plurality of panels sewn to one another and oriented to overlap each other and align with the wearer's foot and calf, wherein said panels comprise an external layer of a fabric material sewn to an internal layer of a fleece material, wherein a plurality of fastener pieces affixed to surfaces of said external and internal layers are arranged to overlap and adhere said plurality of panels to each other, and wherein a pocket space adapted to longitudinally align to the wearer's calf is configured between said external and internal layers; and
   b) a foam support comprising;
      i) a cradle piece having a longitudinal channel adapted to mount about the wearer's calf, wherein said cradle piece is inserted into said pocket space, wherein a posterior surface of said cradle piece is flat, wherein a longitudinal recessed anterior surface of said cradle piece in said channel opposite the flat posterior surface exhibits a contoured portion shaped to elevate the wearer's calf, wherein an arcuate cutout is defined through said posterior and anterior surfaces of said cradle piece at an end of said cradle piece adapted to lie posterior to the wearer's heel, and
      ii) an extension piece comprising an elongated foam sheet bonded to the flat posterior surface of said cradle piece adjacent said arcuate cutout and inserted between said external and internal layers of fabric and fleece to extend between said external and internal layers of fabric and fleece into a toe panel and adapted to only underlie plantar surfaces of the wearer's heel, sole and toes and fold back upon itself over distal ends of the wearer's toes and an anterior surface of the wearer's foot.

2. Footwear apparatus as set forth in claim 1 wherein said plurality of fastener pieces comprise a plurality of tabs of hook and loop fastener material arranged to directly secure said plurality of panels to each other and cover the calf and foot.

3. Footwear apparatus as set forth in claim 2 including a strap having tabs of hook and loop fastener material affixed to said strap and mountable to the fasteners affixed to said plurality of panels.

4. Footwear apparatus as set forth in claim 2 including a right triangle shaped support having a fastener affixed to a surface of the support and mountable to the fasteners affixed to said plurality of panels.

5. Footwear apparatus as set forth in claim 1 wherein said cradle piece and extension piece comprise a closed cell foam material and wherein a portion of said extension piece underlying the wearer's sole is covered with a layer of open celled foam.

6. Footwear apparatus as set forth in claim 1 including a recess in the flat posterior surface of said cradle piece and wherein an end of said extension piece is bonded to the cradle piece in said recess.

7. Footwear apparatus as set forth in claim 1 wherein the suspension of the wearer's heel in a space defined between the arcuate cutout in the cradle piece and the extension piece limits heel pressure with the internal layer of fleece, cradle piece and extension piece to an average pressure in the range of 10 to 15 mmHg.

8. Footwear apparatus as set forth in claim 1 wherein said arcuate cutout exhibits a generally inverted U-shape and wherein an end of said extension piece is joined to said cradle piece in a recess in the flat posterior surface of said cradle piece adjacent said inverted U-shaped cutout.

9. Therapeutic footwear apparatus for covering a wearer's leg comprising:
   a) a boot comprising a plurality of panels sewn to one another and oriented to overlap each other and align with a wearer's foot and calf, wherein said plurality of panels include first and second calf panels, first and second foot panels and a toe panel, wherein said first and second foot panels extend from said first and second calf panels, wherein said toe panel extends from and exhibits a width less than said first and second foot panels, wherein said plurality of panels comprise an external layer of a fabric material sewn to an internal layer of a fleece material, wherein a plurality of fastener pieces are affixed to surfaces of said external and internal layers and arranged to overlap and adhere said plurality of panels together, and wherein a pocket space adapted to longitudinally align to the wearer's calf is configured between said external and internal layers; and b) a foam support comprising;

i) a cradle piece having a longitudinal U-shaped channel adapted to mount about the wearer's calf, wherein said cradle piece is inserted into said pocket space, wherein a posterior surface of said cradle piece is flat, wherein a longitudinal recessed anterior surface of said cradle piece in said channel opposite the flat posterior surface exhibits a contoured portion adapted to elevate a posterior surface of the wearer's calf, wherein an arcuate cutout is defined through said posterior and anterior surfaces at an end of said cradle piece and adapted to lie posterior to the wearer's heel, wherein the flat posterior surface includes a recess adjacent said arcuate cutout, and ii) an extension piece comprising an elongated foam sheet bonded to the recess at the flat posterior surface of said cradle piece, wherein said extension piece extends between said external and internal layers of fabric and fleece and through said first and second foot panels into the toe panel and adapted to only underlie plantar surfaces of the wearer's heel, sole and toes and fold back upon itself over distal ends of the wearer's toes and an anterior surface of the wearer's foot, and wherein said extension piece comprises first and second foam layers.

10. Footwear apparatus as set forth in claim 9 including a strap having tabs of hook and loop fastener material affixed to said strap and mountable to the fasteners affixed to said plurality of panels.

11. Footwear apparatus as set forth in claim 9 including a right triangle shaped support having a fastener affixed to a surface of the support and mountable to the fasteners affixed to said plurality of panels.

12. Therapeutic footwear apparatus for covering a wearer's leg comprising:

a) a boot comprising a plurality of panels sewn to one another and oriented to overlap each other and align with a wearer's foot and calf, wherein said plurality of panels include first and second calf panels, first and second foot panels and a toe panel, wherein said first and second foot panels extend from said first and second calf panels, wherein said toe panel extends from and exhibits a width less than said first and second foot panels, wherein said plurality of panels comprise an external layer of a fabric material sewn to an internal layer of a fleece material, and wherein a plurality of fastener pieces are affixed to surfaces of said external and internal layers and arranged to overlap and adhere said plurality of panels together; and b) a foam support comprising;

i) a cradle piece having a longitudinal U-shaped channel adapted to mount about the wearer's calf, wherein said cradle piece is mounted in said first and second calf panels between said external and internal layers of fabric and fleece, and ii) an extension piece comprised of an elongated layer of foam bonded to a posterior surface of said cradle piece and adapted to mount adjacent in the wearer's heel, wherein said extension piece is mounted between said external and internal layers of fabric and fleece and is oriented to extend through said first and second foot panels and into said toe panel and is adapted to only underlie the plantar surfaces of the wearer's heel, sole and toes and fold back upon itself over the distal ends of the wearer's toes; and c) wherein said toe panel includes a plurality displaced transverse rows of stitching adapted to permit trimming the toe panel without fraying to size the boot to the wearer.

* * * * *